United States Patent [19]

Schneider

[11] Patent Number: 5,713,879
[45] Date of Patent: Feb. 3, 1998

[54] DEVICE FOR COLLECTING AND FILTERING BLOOD

[75] Inventor: Lothar Schneider, Rheinau, Germany

[73] Assignee: Metec A. Schneider GmbH, Willstätt, Germany

[21] Appl. No.: 779,474

[22] Filed: Jan. 7, 1997

Related U.S. Application Data

[63] Continuation-in-part of Ser. No. 394,282, Feb. 24, 1995, abandoned.

[30] Foreign Application Priority Data

Feb. 26, 1994 [DE] Germany .................... 9403245 U

[51] Int. Cl.$^6$ .................................................. A61M 1/00
[52] U.S. Cl. .................................................. 604/319
[58] Field of Search .................... 604/317, 318, 604/319, 406, 408; 128/760, 762

[56] References Cited

U.S. PATENT DOCUMENTS

| | | |
|---|---|---|
| 3,492,991 | 2/1970 | Dyer . |
| 4,111,204 | 9/1978 | Hessel . |
| 4,306,557 | 12/1981 | North . |
| 4,744,785 | 5/1988 | Rosenthal et al. . |
| 4,772,256 | 9/1988 | Lane et al. . |
| 4,798,578 | 1/1989 | Ranford . |
| 4,870,975 | 10/1989 | Cronk .................... 604/319 |
| 5,149,325 | 9/1992 | Telang . |
| 5,158,533 | 10/1992 | Strauss . |
| 5,185,007 | 2/1993 | Middaugh .................... 604/319 |
| 5,269,924 | 12/1993 | Lindsay . |
| 5,382,244 | 1/1995 | Telang . |
| 5,427,836 | 6/1995 | Yamada . |
| 5,470,324 | 11/1995 | Cook et al. . |

FOREIGN PATENT DOCUMENTS

| | | |
|---|---|---|
| 0525493A1 | 7/1992 | European Pat. Off. . |
| 39 04 164 | 2/1989 | Germany . |
| 12033 | 8/1991 | WIPO . |

*Primary Examiner*—Michael J. Milano
*Attorney, Agent, or Firm*—Collard & Roe, P.C.

[57] ABSTRACT

A device for collecting and filtering blood from a surgical site during an operation and returning the blood to the patient after further treatment in a separate treatment apparatus. The device includes a cylindrical container and a cover assembly with a correspondingly sized cover. An expandable plastic pouch extends from the cover into the container. A filter screen is provided within the pouch to coarsely filter incoming blood. A compressed air source is connected to a suction pipe to produce a vacuum within the container. Collected blood may be drawn off by a hose within the pouch leading to a separate treatment device, or may be drained from the bottom of the pouch.

7 Claims, 3 Drawing Sheets

DEVICE FOR COLLECTING AND FILTERING BLOOD

This is a continuation-in-part of application Ser. No. 08/394,282 filed on Feb. 24, 1995 now abandoned.

BACKGROUND OF THE INVENTION

1. Field of the Invention

The invention relates to a device for collecting and coarsely filtering blood from a surgical site. The blood collected is then available for the patient during the operation following treatment by a treatment device installed downstream. The device includes a cylindrical container with a removable cover, an expandable pouch with a filtering screen and a suction hose disposed on the cover.

2. The Prior Art

During surgery, a great quantity of blood is collected at the surgical site. The blood is sucked off and discarded. However, this blood could be of value to the patient, particularly in view of supplying the patient with donor's blood. It has been proposed to suck off the blood and to treat it in such a way that it can be resupplied to the patient.

EP-A-O 345 831 describes an autotransfusion device for collecting blood and other body fluids. The device consists of a solid, vacuum-stable container, which can be evacuated via an outlet opening in the cover or an opening in the bottom part. A membrane is mounted on the top edge of the container. The membrane alternately rests against the inside contour of the cover and the inside of the bottom part. The connection between the edge of the membrane and the bottom or cover is established by fusing the plastic to form a one-piece, one-way container. When the container is completely filled with blood, the membrane assumes substantially the same contour as the container. Also, a connection is provided on the side of the container for vacuum or excess pressure. For repeated use, the parts of the known autotransfusion device have to be dismantled and cleaned, which is relatively costly.

SUMMARY OF THE INVENTION

It is, therefore, an object of the present invention to overcome the drawbacks of the prior art and to provide a device for simply collecting blood during an operation and screening it for coarse particles.

It is a further object of the present invention to provide a device in which most of the parts are discarded after a single use.

These and other related objects are achieved according to the invention by a device for collecting and filtering blood from a surgical site and returning the blood to the patient after further treatment in a separate treatment apparatus. The device consists of a purely cylindrical container and a separate cover assembly. The cover assembly includes a cover removably connected to the container and an expandable plastic pouch attached thereto for storing and temporarily transporting the blood. The plastic pouch extends from the cover into the container and forms a space therebetween. A filter screen is attached to the cover and extends within the pouch for coarsely filtering the incoming blood. The cover has short pipes protruding above it to connect to the patient. The short pipes extend through apertures in the cover into the space within the filter screen. A suction pipe is coupled to the cover and includes a suction outlet extending above the cover and another outlet extending between the container and the pouch. The cover also has a bore therethrough to connect the suction pipe to the space inside the pouch. This arrangement equalizes the pressure between the inside of the pouch and the space between the pouch and container.

An advantage afforded by the invention is that the separate cover assembly includes all of the important parts, which can be used once and then discarded. The simple cylindrical container can be easily cleaned and reused, whereas the cover assembly with the plastic pouch which actually contacts the blood, is disposable. With the prior art devices, the blood is forced out of the membrane into the container by pressurization, which does not occur with the invention. In addition, all of the parts for maintaining equalized pressure and for suction off the blood are located on the cover. Therefore, no suction parts need to be provided on the container itself, which makes the container easier to clean.

An O-ring is attached to the underside of the cover to provide an air-tight seal between the cover and the container. The cover is tightly locked onto the container by a lock, for example, a bayonet lock. The pouch extends from the cover down to the bottom of the container and includes an angled lower portion. The angled lower portion causes the blood to collect in the lowest point of the pouch so that it can be completely removed for further treatment. To remove the blood from the pouch, a hose is provided which passes through the cover and into the pouch. One end of the hose is connected to a separate treatment device, and the other extends down into the lower portion of the pouch. The hose is anchored in the lower portion of the pouch and contains a plurality of apertures in the bottom section to receive the collected blood and transport it to the treatment device. The container is made from a material which can be sterilized by autoclaving, for example, a polycarbonate.

Since the pouch that holds the blood is removable from the container, the pouch and thus the blood is more easily transportable.

BRIEF DESCRIPTION OF THE DRAWINGS

Other objects and features of the present invention will become apparent from the following detailed description considered in connection with the accompanying drawings which disclose an embodiment of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION OF THE PREFERRED EMBODIMENTS

Figure 1:
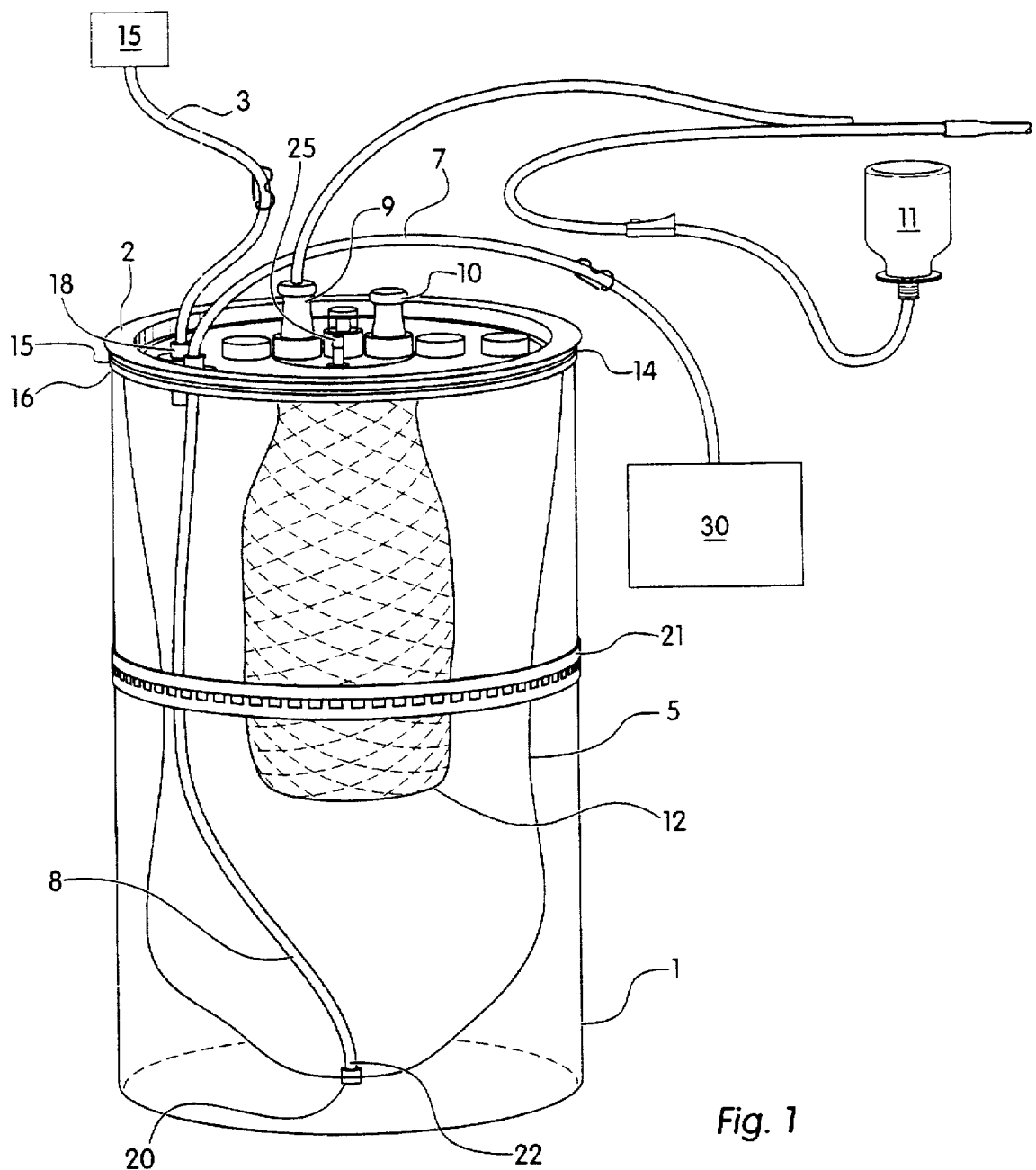
FIG. 1 is a perspective view of the device according to the invention.

Referring now in detail to the drawings, and in particular FIG. 1, there is shown a cylindrical container 1 made of polycarbonate, which can be sterilized in an autoclave. In the center, container 1 is reinforced with ring 21 so that it can be placed on an infusion rack. A cover 2 for container 1 has an underside with a slightly recessed plastic pouch 5 for collecting the blood. An O-ring 14 provides an air-tight seal between container 1 and cover 2. The cover is secured by a bayonet lock consisting of a cover locking element 15 and a container locking element 16. When cover 2 is closed, plastic pouch 5 is completely disposed within the interior of container 1.

A filter screen 12 located on the underside of cover 2, extends into pouch 5. Connection points 9 and 10 are located on cover 2 above filter screen 7 and connect the device to a patient. An infusion device 11 supplies the blood with certain substances, e.g., heparin.

Figure 2:
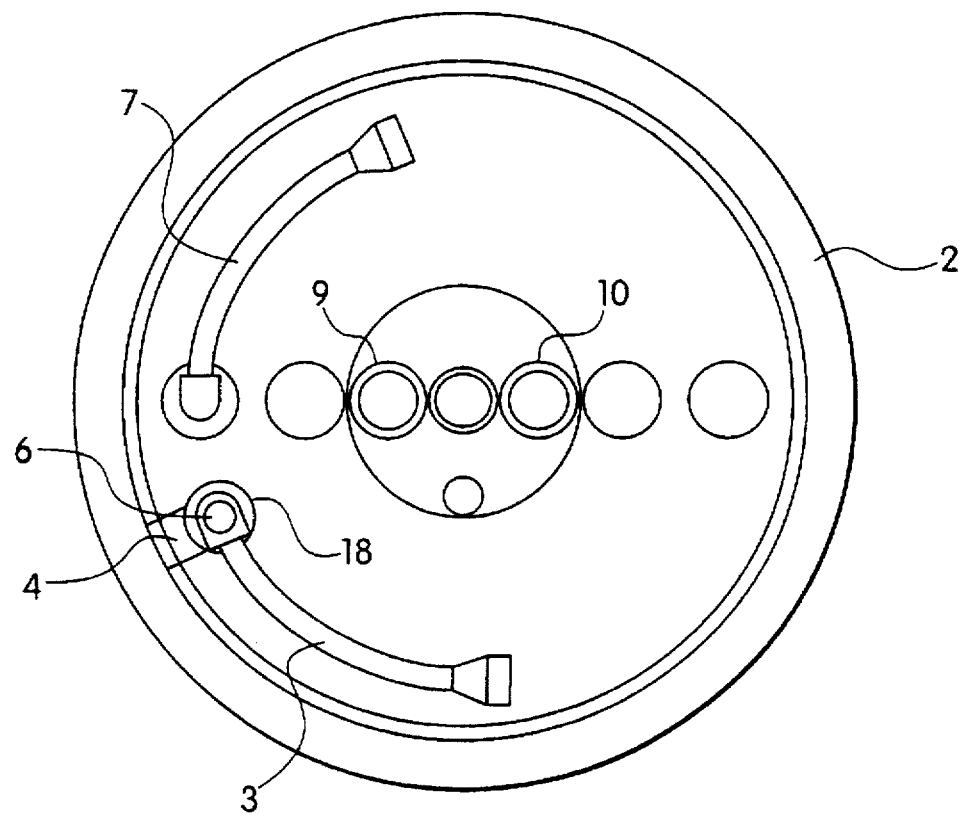
FIG. 2 is a top view of the cover of the device according to the invention.
Figure 3:
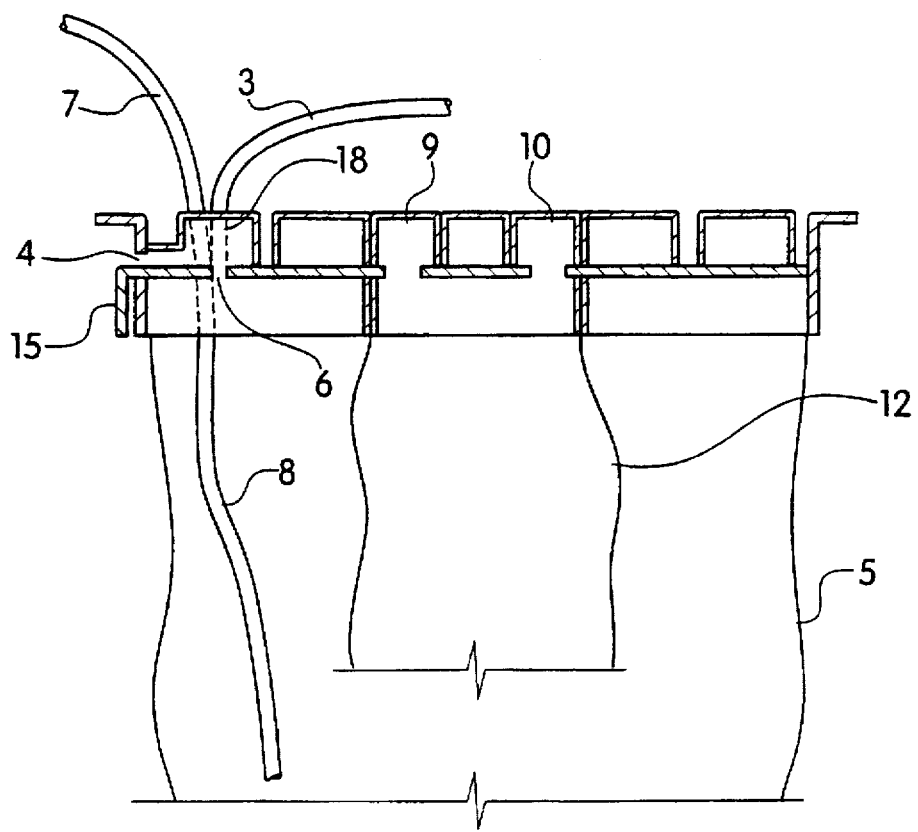
FIG. 3 is an enlarged side view of the blood-collecting pouch and the cover of the embodiment of FIG. 1.

Cover 2 includes a suction pipe 18 for connection to a vacuum source. Pipe 18 is connected to a bore 6 that extends within or below cover 2 and terminates in the space within pouch 5, as shown in FIG. 2. Suction pipe 18 also contains an outlet opening 4 that extends through the cover 2 into the space between container 1 and pouch 5, as shown in FIG. 3. The outlet opening 4 and bore 6 serve to equalize the pressure between the inside of pouch 5 and the space between pouch 5 and container 1. Suction pipe 18 is connected via a hose 3 to the hospital's internal compressed air system 15. Cover 2 is also equipped with an entry valve 25, for injecting necessary drugs into the pouch to mix with the collected blood.

The bottom of pouch 5 is angled and comes to a point. A hose 8 extends down into the deepest part of pouch 5 and is anchored at the bottom of pouch 5. Hose 8 extends through cover 2 for connection via tube 7 to the separate blood treatment device 30. Hose 8 has a plurality of apertures 22 for receiving collected blood and transporting the blood to treatment device 30. On the lower end of pouch 5 at the point where hose 8 is anchored, a discharge device 20 is provided for draining blood from hose 8 and pouch 5 if the blood is not to be sent directly to treatment device 30.

Figure 4:
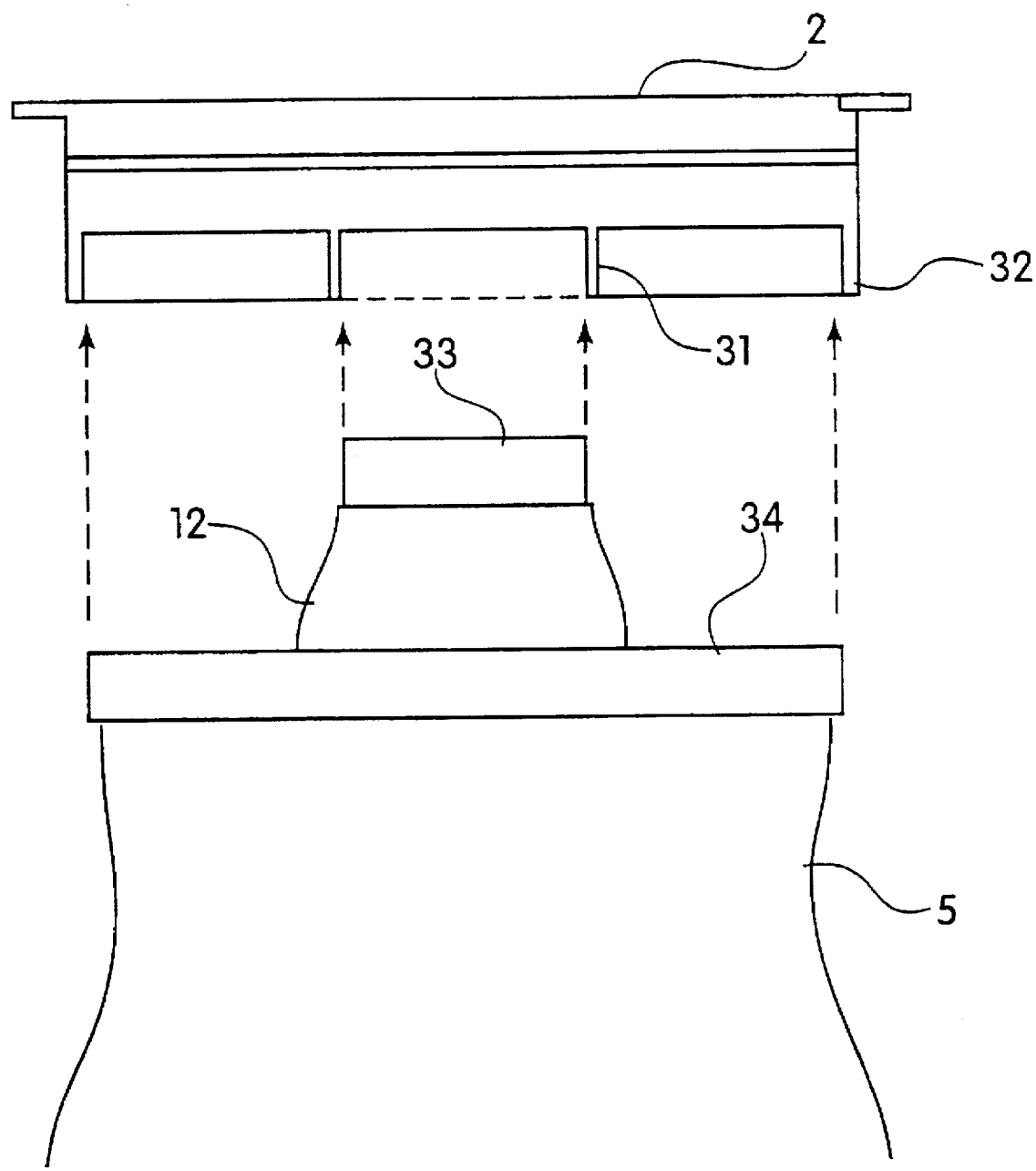
FIG. 4 is an exploded view of the connection point of the pouch and filter screen to the cover.

Filter screen 12 and pouch 5 are manufactured tightly fastened to cover 2. The tight fastening of filter 12 and plastic pouch 5 is shown in FIG. 4.

On the underside of cover 2, there is provided a circular flange 31 having a smaller diameter, and an additional flange 32, having a diameter the size of the outer circumference of the rim of cover 2.

In the upper rim of filter screen 12, a cylinder ring 33 is inserted for fastening filter 12 to cover 2. The diameter of cylinder ring 33 corresponds approximately to the inner diameter of flange 31. The upper rim of filter 12 is pulled over cylinder ring 33 under tension. Ring 33 is then pressed with filter 12 firmly into the inside of flange 31 and connected tightly thereon via known means.

A second cylinder ring 34 is provided in a similar fashion, whose outer diameter corresponds approximately to the inner diameter of flange 32. In the same way, as with filter 12, the upper rim of pouch 5 is pulled over cylinder ring 34 under tension, and cylinder ring 34 is then pressed into the inside of flange 32. The tight fastening may then be supplemented with usual and known means. In this manner, the device according to the invention may be manufactured quickly and easily.

The capacity of container 1 is approximately 3,000 ml. Filter screen 12 has a mesh width of 170 microns.

While only a single embodiment of the present invention has been shown and described, it is to be understood that many changes and modifications may be made thereunto without departing from the spirit and scope of the invention as defined in the appended claims.

What is claimed is:

1. A device for collecting and filtering blood from a surgical site during an operation and returning the blood to the patient after further treatment in a separate treatment apparatus, the device comprising:

a purely cylindrical container; and a separate, disposable cover assembly including:
 (i) a cover removably connected to said container;
 (ii) expandable receiving means for storing and temporarily transporting the blood, comprising a plastic pouch extending from said cover into said container and forming a space between said pouch and said container;
 (iii) a filter screen extending within said pouch;
 (iv) a suction pipe coupled to said cover with a suction pipe outlet extending above said cover;
 (v) a duct connected to said suction pipe and extending through said cover and opening into the space within said pouch; and
 (vi) an outlet opening connected to said duct and opening into the space between the pouch and the cylindrical container to equalize the pressure between the interior of the pouch and the space between the pouch and the container;

wherein blood from a patient is received through said cover, enters the filter screen and passes through said filter screen to be stored in said pouch and wherein the receiving means, filter screen, suction pipe, duct and outlet opening are disposed entirely on the cover.

2. The device according to claim 1, comprising:

an O-ring attached to said cover to provide a seal between said cover and said container; and means for locking said cover to said container, comprising a bayonet lock.

3. The device according to claim 1, wherein said pouch extends to said container bottom and includes an angled lower portion.

4. The device according to claim 3, further comprising:

a separate treatment device;

a hose passing through said cover and having two ends, one end connected to the separate treatment device and the other end extending into the lower portion of the pouch and anchored at said lower portion, said other end having a plurality of apertures for receiving collected and filtered blood, wherein blood collected in the pouch is transported through the hose and into the separate treatment device.

5. The device according to claim 1, wherein said container is made of a polycarbonate material which can be sterilized by autoclaving.

6. The device according to claim 3, comprising a discharge valve disposed along the bottom of said pouch and connected to said hose, for selectively draining blood from said pouch through said hose.

7. The device according to claim 1, further comprising first and second circular flanges arranged on the underside of the cover;

a first cylinder ring attached to the top of the expandable receiving means, said first cylinder ring having a diameter corresponding to the inner diameter of the first circular flange; and a second cylinder ring attached to the top of the filter screen, said second cylinder ring having a diameter corresponding to the inner diameter of the second circular flange, wherein the expandable receiving means and filter screen are mounted on the cover by inserting the first and second cylinder rings into the first and second flanges, respectively.

* * * * *